United States Patent [19]

Brown

[11] Patent Number: 5,481,038
[45] Date of Patent: Jan. 2, 1996

[54] BORANE-N,N-DIISOPROPYLALKYLAMINE HYDROBORATION AGENTS

[75] Inventor: Herbert C. Brown, West Lafayette, Ind.

[73] Assignee: Aldrich Chemical Company, Inc., Milwaukee, Wis.

[21] Appl. No.: 437,585

[22] Filed: May 9, 1995

[51] Int. Cl.$^6$ .................................................. C07F 5/02
[52] U.S. Cl. ............................................................. 568/1
[58] Field of Search ...................................... 568/1

[56] References Cited

U.S. PATENT DOCUMENTS 3,035,891  5/1962  Köster ........................................ 23/14
3,051,754  8/1962  Jenkner ..................................... 260/583
3,358,034  12/1967  Brown ..................................... 260/606.5

Primary Examiner—Porfirio Nazario-Gonzales
Attorney, Agent, or Firm—Joyce R. Niblack; Niblack & Niblack

[57] ABSTRACT

Borane-N,N-diisopropylalkylamines as represented by the formula:

$$H_3B \cdot NPr^i_2R$$

wherein $Pr^i$ is isopropyl, R is branched-chain alkyl or cycloalkyl having 3 to 6 carbon atoms and B is boron are provided. The compounds are new hydroboration agents.

4 Claims, No Drawings

BORANE-N,N-DIISOPROPYLALKYLAMINE HYDROBORATION AGENTS

BACKGROUND OF THE INVENTION

1. Field of Invention

The present invention provides a novel class of borane adducts with selected tertiary diisopropylalkylamines, specifically diisopropylalkylamines wherein the alkyl group is a branched-chain $C_3$–$C_7$ alkyl, and their use in the hydroboration and reduction of organic compounds. The novel borane-amine adducts of this invention have a number of advantages over the presently available agents.

2. Prior Art

Borane adducts with amines are versatile reagents exhibiting many different properties as compared to the metal borohydrides. For example, they are soluble in a variety of solvents, including hydrocarbons or even water, and in some cases can be used in an acidic medium. Many adducts have been synthesized. See for example, Long, L.H. in W.J. Mellor *A Comprehensive Treatise on Inorganic and Theoretical Chemistry;* Longman: London, 1981, Supplement Vol. 5, Part B1, p 1.; and Meller, A. In Gmelin *Handbook of Inorganic and Organometallic Chemistry;* Springer: Berlin, 1992, 4th Supplement, Vol. 3, p 1. Several are commercially available. They find various uses, e.g., as fuel additives, polymerization catalysts, polymer stabilizers and stain removers, in metal plating and in the dye and pharmaceutical industries. See Lane, C.F. *Aldrichimica Acta* 1973, 6, 51. Most of these applications are based on their reducing properties.

In contrast, the use of borane-amine adducts for hydroboration is rather limited due to strong complexation, which renders their reactivity low as compared to the weak borane adducts with ethers and Gulfides. For example, boranetriethylamine does not hydroborate 1-octene at room temperature and only very slowly in refluxing tetrahydrofuran (THF). See Brown, H.C. et al. *Inorganic Chem.* 1984, 23, 2746.

Amines as borane carriers offer significant advantages often giving adducts of low sensitivity to moisture and air and readily soluble in representative solvents. Environmentally important is an easy recovery of the amine from the hydroboration products, making possible its ready recycling. The significance of these factors becomes apparent with the growing importance of diborane for the synthesis of pharmaceuticals and other valuable compounds. However, the well established reagents, boranetetrahydrofuran and borane-dimethylsulfide (BMS) suffer a number of disadvantages for large-scale commercial applications as discussed below.

Borane-tetrahydrofuran is a valuable reagent for the hydroboration of olefins and for the reduction of organic compounds. It suffers from the disadvantage in that the solutions are unstable over a period of time. U.S. Pat. No. 3,882,037 discloses stabilized borane-tetrahydrofuran solutions which permit storage of such solutions for relatively longer periods of time. However, the inherent availability only as a relatively dilute solution in tetrahydrofuran largely restricts its use to tetrahydrofuan solutions and poses a drawback to commercial use of this reagent.

Borane-methyl sulfide (BMS) is much more stable than borane-tetrahydrofuran and is widely used for both hydroboration and reduction [See Burg et al., *J. Am. Chem. Soc.* 76, 3307 (1954) and Coyle et al., *J. Am. Chem. Soc.* 81, 2989 (1959)]. However, it suffers from the serious disadvantage in that it yields a product which contains free dimethyl sulfide.

The free dimethyl sulfide is highly volatile, b.p. 38° C., flammable and has a very noxious odor. Moreover, it is not soluble in water, so it cannot be disposed of by washing it away with water which poses a serious environmental problem.

Borane-1,4-thioxane (U.S. Pat. No. 4,298,750) is another valuable hydroboration agent. It has both lower volatility and milder odor than dimethyl sulfide. It has a limited solubility in water and can be easily oxidized to the corresponding sulfoxide, which is miscible in water. This agent is a liquid, 8M in $BH_3$, stable over prolonged periods. Unfortunately, this commercially available reagent is relatively costly compared to borane-tetrahydrofuran and borane-dimethyl sulfide.

The growing importance of borane reagents for the synthesis of pharmaceuticals and other compounds and the problems associated with other well established borane adduct hydroboration agents, e.g., low concentration and stability, high volatility, flammability, unpleasant odor, as discussed above, create a need for easy to handle, stable and environmentally benign hydroborating agents as discussed specifically below.

Thus, the search continues for effective, versatile borane derivatives which are as effective as the commercially available reagents but which overcome the disadvantages of noxious odor, expense, volatility, and lack of water solubility. The amines of the present invention are well suited for that purpose. They have an agreeable odor, form neat adducts, are highly concentrated in borane, are soluble in various solvents, and the amine can be readily removed and recovered from hydroboration products.

Although many borane-amine adducts are known, almost all amines used for their preparation are relatively unhindered and hence strongly complexing, producing borane adducts which exhibit a low reactivity for hydroboration at room temperature. See C.F. Lane, *Aldrichimica Acta*, 6, 51 (1973). On the other hand, it has been reported that highly hindered 1,2,2,6,6-pentamethylpiperidine does not form a borane adduct. See Flores-Parra, N. et al., *Tetrahedron Lett.*, 47, 6903 (1991).

It is wholly surprising that the borane- N,N-diisopropylalkylamines of the present invention are valuable hydroborating agents since the ethyl derivative is a hindered amine widely used as a proton scavenger [Raber, D.J. et al., Tetrahedron Lett., 4741 (1971)] but which forms a borane adduct that only slowly hydroborates 1-octene in tetrahydrofuran at room temperature. The compounds of this invention, on the other hand, hydroborate 1-octene in tetrahydrofuran at room temperature in less than anhour, and in most cases in 15–30 minutes.

SUMMARY OF THE INVENTION

The present invention provides novel borane adducts of N,N-diisopropylalkylamines, as represented by the formula:

wherein $Pr^i$ is isopropyl, R is branched chain alkyl or cycloalkyl having 3 to 7 carbon atoms and B is boron.

Presently preferred compounds are those wherein R is isopropyl, sec-butyl or isobutyl.

Generally speaking, the novel compounds of this invention are conveniently prepared in a straight-forward procedure by passing diboraneinto a neat amine at 0° C. in a bubbler provided with a stirrer. Excess diborane not absorbed by the amine is absorbed in a down-stream bubbler containing tetrahydrofuran over mercury and cooled in ice water. A mercury bubbler is connected to the exit. Diborane is passed into the amine until the concentration of excess borane in THF reaches approximately 1M. The borane-amine adduct is stirred overnight at room temperature prior to disconnecting the bubblers and analyzed for active hydride following the procedure described by Brown, H.C., *Organic Syntheses via Boranes*, J. Wiley: New York, 1975, p. 191, using a 2M hydrochloric acid-glycerol-water (2:1:1) hydrolysis solution.

In the practice of the invention, borane adducts of N,N-diisopropylalkylamines are prepared by passing diborane into a neat amine until no more diborane is absorbed. The adduct with N,N-diisopropylisobutylamine is liquid above 0° C., 4.6M in borane, and is stable over prolonged periods at room temperature. The adduct with N,N-diisopropyl-sec-butylamine is a liquid 3.3M in borane when freshly prepared at 0° C., slowly losing borane at room temperature. All of the adducts of this invention hydroborate 1-octene in tetrahydrofuran at room temperature in less than 1 hour to give trioctylborane. They are also soluble in diethyl ether and dichloromethane. Alternatively, neat adducts can be used for hydroboration.

The following examples further illustrate the invention.

DETAILED DESCRIPTION OF PREFERRED EMBODIMENTS

All manipulations and reactions with air-sensitive compounds were carried out under nitrogen atmosphere. All glassware was oven-dried for several hours, assembled while hot and cooled in a stream of dry nitrogen gas. Syringes were assembled and fitted with needles while hot. Techniques for handling air-sensitive compounds under nitrogen atmosphere are described in Brown, H.C., *Organic Syntheses Via Boranes*, J. Wiley; New York, 1975, p. 191. $^1$H, $^{13}$C and $^{11}$B NMR spectra were recorded on a Varian Gemini 300 multinuclear instrument. The $^{11}$B NMR chemical shifts are $\delta$ relative to $BF_3.OEt_2$. Mass spectra were taken on a 4000 Finnigan MAT spectrometer. Optical rotations were measured on a Rudolph automatic polarimeter Autopol III. GC analyses were carried out on a Varian 3300 chromatograph (catharometer) using a 12 ft×0.125 in column packed with 10% SE-30 polyethylene glycol (Union Carbide) on Chromosorb W 100–120 mesh). Microanalysis were performed at the Microanalytical Laboratory, Purdue University, West Lafayette, Ind., USA.

Diisopropylethylamine and triisobutylamine were commercial products (Aldrich Chemical Company, Milwaukee, Wis.). Tetrahydrofuran was freshly distilled from benzophenone ketyl prior to use.

EXAMPLE 1

N,N-Diisopropylisobutylamine

A mixture of diisopropylamine (20.24 g, 0.2 mol) and isobutyl phenylsulfonate (29.83 g, 0.1 mol) was refluxed with stirring for 72 hours. Aqueous 5M potassium hydroxide (30 ml, 0.15 mol) was added. The organic phase was separated and the aqueous phase was extracted with n-pentane (50 ml). The organic solutions were combined, dried over anhydrous magnesium sulfate and the produce was isolated by distillation to yield 10.70 g, 68% of the title product, bp 75–77° C./45 mm Hg. $^1$H NMR CDCl$_3$ $\delta$ ppm, 0.83 (d, J=6.5 Hz, 6H, CH$_3$), 0.95 (d, J=6.5 Hz, 12H, CH$_3$), 1.59 (nonet, J=6.5 Hz, 1H, CH), 2.10 (d, J=6.5 Hz, 2H, CH$_2$), 2.95 (sep, J=6.5 Hz, 2H, CH).

EXAMPLE 2

N,N-Diisopropylmethallylamine

A mixture of diisopropylamine (20.24 g, 0.2 mol), methallyl chloride (9.00 g, 0.1 mol), adiponitrile (10.81 g, 0.1 mol) and tetrabutylammonium iodide (3.69 g, 10 mmol) was refluxed for 5 h with vigorous stirring (two phases). The temperature of the mixture increased from 88° to 125° C. Potassium hydroxide solution (5M, 15 ml, 0.15 mol) was added. Three layers formed. The mixture was extracted with n-pentane (2×50 ml). Adiponitrile (the middle layer) was recovered. The pentane solution was dried with anhydrous magnesium sulfate and the product was isolated by distillation: 12.58 g (81%), bp 75–77° C/45 mm Hg. $^1$H NMR CDCl$_3$ $\delta$ ppm, 0.98 (d, J=6.6 Hz, 12H, CH$_3$), 1.70 (s, 3H, CH$_3$), 2.97 (m, 4H, CH$_2$, CH), 4.78 (s, 1H,=CH$_2$), 4.93 (m, 1H,=CH$_2$).

EXAMPLE 3

N,N-Diisopropylisobutylamine By the Reduction of N,N-Diisopropylmethallylamine Diisopropymethallylamine (15.53 g, 0.1 mol) and Raney nickel catalyst (5.00 g, slurry in ethanol) was added to a solution of potassium hydroxide (1.00 g) in anhydrous ethanol (30 ml). The mixture was hydrogenated at 40°–50°C. with stirring under normal pressure until absorption of hydrogen ceased. (~20 h). The solution was decanted from the catalyst, water (100 ml) was added and the product was extracted with n-pentane (2×25 ml), dried with magnesium sulfate and isolated by distillation to yield 16.49 g, 94% yield of the title compound, bp 75°–77° C./45 mm Hg).

EXAMPLE 4

N,N-Dttsopropylbutyramtde

Isobutyryl chloride (10.65 g, 0.1 mol) was added dropwise with stirring to diisopropylamine (20.24 g, 0.2 mol) and the mixture was stirred for 1 h at room temperature. The solid product was filtered off and crystallized from diethyl ether, yield 15.59 g, 91%, mp 34°–35° C.

EXAMPLE 5

N,N-Diisopropylisobutylamine by the Reduction of N,N-Diisopropylbutyramide

A solution of N,N-diisopropylbutyramide (8.57 g, 50 mmol) in tetrahydrofuran-dichloromethane (4:1) was added to borane-tetrahydrofuran (50 ml, 50 mmol). After 1 hour, the mixture was refluxed for 1.5 hours. Water (5 ml) was slowly added, followed by 3M normal hydrochloric acid (40 ml). Organic solvents were distilled off and solid sodium hydroxide (12.00 g, 0.3 mol) was added. The product was extracted with diethyl ether (2×10 ml), dried with magnesium sulfate and isolated by distillation to yield 6.90 g (89%), bp 58°–59° C./19 mm Hg.

EXAMPLE 6

2-(Diisopropylamino)propionitrile

Anhydrous magnesium sulfate (12.04 g, 0.1 mol) was added to diisopropylamine (12.14 g, 0.12 mol), followed by lactonitrile (7.73 g of 92% aqueous solution, 0.1 mol) added all at once with stirring. The reaction mixture spontaneously warmed up to 51° C. It was left overnight at room temperature. Diethyl ether (50 ml) was added, and magnesium sulfate was filtered off and washed with ether (50 ml). The product was isolated by distillation, 11.57 g, 75% yield, bp 49°–50° C./0.1 mm Hg. $^1$H NMR CDCl$_3$ δ ppm, 1.02 (d, J=6.5 Hz, 6H, CH$_3$), 1.17 (d, J=6.5 Hz, 6H, CH$_3$), 1.41 (d, J=6.5 Hz, 3H, CH$_3$, 3.21 (sep, J=6.5 Hz, 2H,=CH) , 3.89 (q, J=6.5 Hz, 1H, CH) .

EXAMPLE 7

Triisopropylaxnine

A solution of 2-(diisopropylamino)propionitrile (15.43g, 0.1 mol) in diethyl ether (25 ml) was added dropwise with stirring to a suspension of methyl magnesium chloride (22.33 g, 0.3 mol) in diethyl ether (250 ml) at reflux. The mixture was refluxed for 30 min after completing the addition and left overnight at room temperature. Water (100 ml) was slowly added and the ether solution was decanted from the solids, which were treated with potassium hydroxide (100 ml, 1 mol) and the mixture was steamed distilled. The distillate was extracted with diethyl ether (100 ml) and the extract combined with the decanted solution and dried over anhydrous magnesium sulfate. The product was isolated by distillation: 7.88 g, 55%, bp 139°–140° C. $^1$H NMR CDCl$_3$ δ ppm, 0.99 (d, J=6.5 Hz, 18H, CH$_3$), 3.11 (sept, J=6.5 Hz, 3H, CH).

EXAMPLE 8

N,N-Diisopropyl-sec-butylamine

A solution of 2-(diisopropylamino)propionitrile (25.00 g, 0.162 mol) in diethyl ether (20 ml) was added dropwise to a 1M solution of ethyl magnesium bromide in diethyl ether (32.4 ml, 0.324 mol) and the mixture was refluxed for 30 min. Water (25 ml) was added and white precipitate was filtered off and washed with diethyl ether (2×100 ml). The ether solutions were combined, dried over anhydrous magnesium sulfate and the product was isolated by distillation: 13.80 g, 51%, bp 60°–62° C./20 mm Hg. $^1$H NMR CDCl$_3$ δ ppm, 0.85 ( t, J=6.5 Hz, 3H, CH$_3$) , 0.98 (d, J= 6.5 Hz, 6H, CH$_3$) 0.99 (d, J=6.5 Hz, 3H, CH$_3$), 1.05 (d, J=6.5 Hz, 6H, CH$_3$) , 1.17–1.44(m, 2H, CH$_2$), 2.70 (m, 1H, CH), 3.08 (sep, J=6.5 Hz, 2H, CH).

EXAMPLE 9

Quantitative Generation of Diborane

A 50-ml one-neck, round-bottom flask provided with a septum inlet, magnetic stirring bar and an adapter with a stopcock was charged with boron trifluoride-diglyme or -triglyme adduct (75 mmol). A 2M solution of sodium borohydride in triglyme (28.5 ml, 57 mmol) was added dropwise by means of a hypodermic syringe. Generation of diborane is smooth and the reaction is not exothermic. After the addition was completed, the flask was heated to 100° C. and kept at this temperature for 15 min. Diborane was absorbed in tetrahydrofuran (30 ml) at 0° C. Analysis of the BH$_3$.THF solution obtained for active hydride according to a standard procedure described in Brown, H.C., *Organic Syntheses via Boranes;* J. Wiley: New York, 1975, p. 241, showed 2.37M concentration of borane (95% yield); $^{11}$B NMR, δ, + 1.0 ppm.

EXAMPLE 10

General Procedure for Preparation of BoraneDiisopropylmonoalkylamine Adducts Diborane (Example 9) was passed into a neat amine (50 mmol) at 0° C., contained in a flask fitted with a sintered glass inlet, a magnetic stirring bar and an exit bubbler. Excess diborane not absorbed by the amine passed through the mercury in the bubbler and dissolved in the next bubbler containing tetrahydrofuran (10 ml) overlaying the mercury, cooled in ice water. A second mercury bubbler was placed in series with the bubbler containing the tetrahydrofuran. Inlet tubes fitted with rubber serum caps were fitted to the flask containing the amine and to the bubbler containing the mercury overlaid with THF so that small samples of the borane-amine and the THF solution containing excess diborane can be removed by hypodermic syringes for analysis without opening the system to the atmosphere. The entire apparatus was flushed with nitrogen or argon and maintained under an inert atmosphere until the preparation of the borane-N,N-diisopropylmonoalkylamine adduct had been completed and the product had been transferred to a suitable storage flask under an inert atmosphere.

Diborane was passed into the amine until the concentration of excess borane in the THF was ~1 M. A small sample of the amine-borane adduct was removed with a hypodermic syringe and analyzed. Then the flask containing the borane adduct was allowed to stand at room temperature and liberation of diborane, if any, noted on the bubbler. Small samples of the borane-amine and the THF solution above the bubbler were removed with syringes and analyzed for active hydrogen using a 2M hydrochloric acid-glycerol-water (2:1:1) hydrolysis solution. This provided information to calculate the molarity of the borane-amine formed at 0° C. and at 25° C. A sample of the amineborane was placed in an NMR tube and the $^{11}$B spectrum determined.

EXAMPLE 11

Borane-N,N-Diisopropylisobutylamine Adduct

In the flask of the apparatus described in Example 10 was placed 50 mmol of N,N-diisopropylisobutylamine (7.68g, 50 mmol). The flask was cooled to 0° C. by immersion in an ice bath. The apparatus was flushed with nitrogen or argon and an inert atmosphere maintained. Diborane, generated as described in Example 9, was passed into the amine until no more was being dissolved. Removal of a small sample of the liquid product with a hypodermic syringe indicated the molarity of the borane in the amine was 4.6. The flask was allowed to warm to room temperature overnight. Only trace amounts of diborane passed through the bubbler. At room temperature, a second aliquot was removed and analyzed. The molarity of the borane was the same: 4.6. The borane and amine were in a ratio of 1:1. A sample of the amineborane was placed in an NMR tube and the $^{11}$B NMR spectrum determined. Only one boron component was present, with δ= -13.51.

A 10-mmol sample of the borane-N,N-diisopropylisobutylamine was added to the THF containing 30 mmol of 1-octene and the reaction followed by $^{11}$B NMR. In 30 minutes, the peak at δ=-13.51 had disappeared and the broad peak characteristic of n-octyl$_3$B had appeared.

EXAMPLE 12

Borane-Triisopropylaumine

The apparatus described in Example 10 was assembled, flushed with nitrogen and a nitrogen atmosphere maintained throughout the process. In the flask was placed 50 mmole of triisopropylamine and the flask cooled to 0° C. Diborane was passed in. At first, absorption was facile, but then a crystalline solid formed and the absorption could not be completed. By adding borane-tetrahydrofuran the crystalline solid, H$_3$CB.NPr$^i$ could be prepared with a 1:1 ratio of boraneamine. The solid exhibited amp 42°–43° C. The $^{11}$B NMR spectrum of the adduct in tetrahydrofuran revealed a single peak at δ= -13.54. In tetrahydrofuran hydroboration of 1-octene by boranetriisopropylamine is fast and complete in 20 minutes forming ntrioctyl borane quantitatively.

EXAMPLE 13

Borane-N,N-diisopropyl-sec-butylamine

In the flask of the apparatus described in Example 10 was placed 50 mmol of N,N-diisopropyl-sec-butylamine. The flask was cooled to 0° C. by immersion in an ice-bath. The apparatus was flushed with nitrogen or argon and an inert atmosphere maintained throughout. Diborane, generated as described in Example 9, was passed into the amine until no more was being dissolved. Removal of a small sample of the liquid product with a hypodermic syringe indicated the molarity of the borane in the amine to be 3.3M. On warming to room temperature, diborane slowly escaped through the mercury bubbler and was trapped by the tetrahydrofuran in the following bubbler. After 24 hr the loss of diborane became negligible. Analysis of the material in the flask change with time. The $^{11}$B NMR spectrum of the adduct in tetrahydrofuran revealed a single peak at δ-5.82. Hydroboration of 3 molar equivalents of 1-octene in tetrahydrofuran by the borane-triisopropylamine adduct was very fast, providing a quantitative yield of n-trioctyl borane in 15 minutes.

EXAMPLE 14

Higher Borane-N,N-Diisopropylmonoalkylamines

Similar results are realized in preparing H$_3$B.Pr$^i$R with 2-methyl-1-butyl and 2-methyl-1-pentyl, 2-pentyl, 2-hexyl, cyclopentyl and cyclohexyl. Consequently, these derivatives are not described in detail herein.

EXAMPLE 15

Hydroboration of Representative Alkenes

The hydroboration characteristics of these new borane adducts are very similar to those previously observed for boranetetrahydrofuran, borane-dimethyl sulfide and borane-1,4-thioxane. Typical terminal olefins such as 1-pentene, 1-hexene, 1-octene, 2-methyl-1-butene, vinylcyclohexene, styrene and the like undergo hydroboration in the ratio of 3 alkene: 1 BH$_3$ to give R$_3$B.

Typical internal alkenes such as 2-butene, 3-hexene, cyclopentene, cyclohexene, cyclooctene, norbornene, and β-pinene undergo hydroboration in the ratio of 3 olefins:1 BH$_3$ to give R$_3$B.

Trisubstituted olefins such as 2-methyl-2-butene, 1-methylcyclopentene, 1-methylcyclohexene, and α-pinene undergo hydroboration to the R$_2$BH stage, i.e. in a ratio of 2 olefins: 1 BH$_3$.

More hindered olefins, such as 2,3-dimethyl-2-butene and 2,4,4-trimethyl-2-pentene, undergo hydroboration in a ratio of 1 olefin: 1 BH$_3$, giving RBH2.

Table 1 compares the properties of selected boraneamine adducts of this invention with representative borane-amine adducts which do not perform as well.

TABLE 1

Selected Borane-Amine Adducts

| | exchange,[a] % | | amine.BH$_3$ | | | | |
|---|---|---|---|---|---|---|---|
| | | | state[b] | [BH$_3$][c] | $^{11}$B NMR[d] | hydroboration of 1-octene[e] | |
| amine | BH$_3$.SMe$_2$ | BH$_3$.THF | (mp, °C.) | M | δ | in THF[f] | neat |
| i-Pr$_2$NEt | 100 | 100 | | | −13.46 | 24 h (38%) | |
| i-Pr$_2$NCH$_2$CH$_2$OMe | 72 | 86 | | | −13.24 | 9 h | |
| i-PrNBu$_2^i$ | 52 | 87 | | | −12.09 | 15 | |
| i-Bu$_3$N | 50 | 88 | solid (60–61) | | −12.05 | 24 | |
| i-Pr$_2$NBu$^i$ | 42 | 87 | liquid | 4.6 | −13.54 | 30 min | 3 h |
| i-Pr$_3$N | 18 | 60 | solid (42–43) | | −15.66 | 20 min | |
| i-Pr$_2$NBu$^s$ | 0 | 30 | liquid | 3.3→2.5 | −5.82[g] | 15 min | 1 h |

[a]Amine mixed with BMS or 1 M BH$_3$.THF in 1:1 molar ratio at room temperature and analyzed by $^{11}$B NMR.
[b]At 0° C.
[c]Estimated by hydrolysis in 2 M HCl-glycerol-water (2:1:1) and measuring hydrogen evolved.
[d]From the exchange with BMS.
[e]5% excess of 1-octene, room temperature.
[f]3 M solution in 1-octene.
[g]From the exchange with BH$_3$.THF.

revealed the molarity to be 2.5M, with negligible further

The invention claimed is:
1. Borane- N,N-diisopropylalkylamines represented by the formula:

$$H_3B \cdot NPr^i_2R$$

wherein $Pr^i$ is isopropyl, R is branched-chain alkyl or cycloalkyl having 3 to 6 carbon atoms and b is boron.

2. A compound of claim 1, borane-N,N-diisopropylisobutylamine.

3. A compound of claim 1, borane-triisopropylamine.

4. A compound of claim 1, borane-N,N-diisopropyl-secbutylamine.

* * * * *